United States Patent [19]

Fox, Jr. et al.

[11] Patent Number: 4,599,226

[45] Date of Patent: Jul. 8, 1986

[54] WOUND DRESSING COMPRISING SILVER SULFADIAZINE INCORPORATED IN ANIMAL TISSUE AND METHOD OF PREPARATION

[75] Inventors: Charles L. Fox, Jr., Sherman, Conn.; Shanta M. Modak, River Edge, N.J.; Paul Fox, Valhalla, N.Y.

[73] Assignee: Genetic Laboratories, Inc., St. Paul, Minn.

[21] Appl. No.: 585,294

[22] Filed: Mar. 1, 1984

Related U.S. Application Data

[62] Division of Ser. No. 480,687, Mar. 31, 1983, Pat. No. 4,446,124.

[51] Int. Cl.⁴ .................. A61K 9/70; A61K 35/12
[52] U.S. Cl. ........................... 424/27; 8/94.11; 424/28; 424/95; 435/1; 514/157
[58] Field of Search ............ 424/95, 229, 27, 28; 435/1; 8/94.11

[56] References Cited

U.S. PATENT DOCUMENTS 3,761,590  9/1973  Fox ........................... 424/229
4,049,802  9/1977  Fox ........................... 424/229

OTHER PUBLICATIONS

Yamashita-Chem. Abst., vol. 89 (1978) p. 80253K.
Fox et al.-Ann. Chir. Plast., vol. XXIV, No. 3 (1979) pp. 265-267.

*Primary Examiner*—Sam Rosen
*Attorney, Agent, or Firm*—Orrin M. Haugen; Thomas J. Nikolai

[57] ABSTRACT

Animal tissue and the like having silver sulfadiazine incorporated therein is useful as a covering for burns and/or wounds. The silver sulfadiazine is incorporated in the tissue by soaking the tissue in an ammoniacal silver sulfadiazine solution or suspension. When the silver sulfadiazine is so incorporated in the tissue via an ammonium solution, more silver is found to be present than would normally be expected and the effectiveness of the thus treated tissue as a wound covering increases.

10 Claims, No Drawings

WOUND DRESSING COMPRISING SILVER SULFADIAZINE INCORPORATED IN ANIMAL TISSUE AND METHOD OF PREPARATION

This is a division of application Ser. No. 480,687, filed Mar. 31, 1983, now U.S. Pat. No. 4,446,124.

BACKGROUND OF THE INVENTION

This invention relates to a process for prearing a dressing or covering for wounds and/or burns. Animal tissue has long been known to be a useful source of material for wound coverings. Although not identical to human skin, the composition and usefulness of some animal tissue resembles human skin. For example, a covering for wounds, ideally, both protects the wound against contact with moisture and external contaminants, while also being permeable to the excretions, in particular, water vapor, which are produced by normal metabolic processes.

Silver sulfadiazine (AgSD) is known as a useful antimicrobial in the treatment of wounds, and of burns in particular, see U.S. Pat. No. 3,761,590 (1973), Fox; Bose, Storing Amniotic Membrane in Silver Sulfadiazine Suspension, The Canadian Medical Association Journal, 127, No. 2, p. 112 (July 15, 1982); Fox, Modak and Stanford, Silver Treated Graft Materials for Coverage of Infected Burn Wounds, Ann. Chir. Plast. 24, N.3, 265–267 (1979).

While animal tissue, and pigskin in particular, satisfies certain criteria for a burn wound covering, there are certain difficulties which militate against using simple, untreated animal tissue as a wound covering. First, and most important of these, is the fact that while animal tissue, when used as a wound covering, may protect the wound against external agents and influences, it does not and cannot prevent infection caused by bacteria, for example, which may have entered the wound prior to the application of the covering, or against whatever bacteria which may enter through the covering. While the problem may be alleviated in part by using a topical bacteriocide (e.g., silver sulfadiazine cream) applied to the skin covering, there is still a chance of infection entering the wound when the dressing must be changed. Such changes must be done with some frequency as the wound cover, even though permeable, will tend to become sodden from topical bacteriocides as well as from metabolic waste products. These changes of dressing allow bacteria to enter, even if the wound is left uncovered for a very short time. Also, while animal tissue is carefully treated so as to attempt to insure that the tissue is initially free of bacteria, sterility cannot be guaranteed, particularly when applied as a wound covering. In particular, should the wound be allowed to be exposed to air, the chance of infection by airborne bacteria is made even greater.

SUMMARY OF THE INVENTION

It has been found that ammoniated or aqueous ammoniated silver sulfadiazine solution incorporated in animal tissue provides an effective dressing for burns and/or wounds. The method of incorporation of silver sulfadiazine in animal tissue may be accomplished in several ways, as described herein. After incorporation of ammoniated silver sulfadiazine with animal tissue takes place, analysis reveals that more silver is incorporated than would be expected. It is thought that the excess incorporation of silver is a result of incorporation of silver ions with collagen molecules within the tissue, although this is uncertain, and the inventors do not bind themselves to this theory.

DETAILED DESCRIPTION OF THE INVENTION

Samples of tissue taken from slaughtered animals are first prepared for later treatment for use as wound dressings. The samples of tissue are selected from redently slaughtered, healthy animals. Preferably, the tissue is taken from animals which have been slaughtered no more than one your prior to tissue selection. Preferred tissues include animal skin, for example, porcine tissue or pigskin, and human ammiotic tissue. The procine tissue is removed via use of clean, sharp knives, and the removed tissue is then placed immediately in cooling containers, and is then transported to a processing laboratory. At such a processing laboratory, the samples are cut to sizes suitable for use as covers for particular wounds and the samples are then ready for the next phase in their preparation as wound dressings.

As different types of injury require different sizes and shapes of dressings, the cleaned tissue is cut to appropriate sizes and shapes. The tissue is then prepared for treatment.

Samples are placed in containers which contain solutions of normal physiological saline. The containers are heat sealed, and then irradiated with either beta or gamma radiation. Such radiation treatment has the effect of both sterilizing and tanning the material. Following radiation treatment, the samples are placed in quarantine freezer storage and then subject to culturing procedures to determine sterility. The culturing procedure involves immersing the tissue in culture medium which has been chosen so as to be conducive to bacterial growth. The tissue is observed for growth of bacteria, and if such growth appears at the end of 14 days or less, the tissue is discarded as not sterile. If such growth is not observed, the tissue is considered sterile, and is deemed suitable for treatment with sulfadiazine and solutions containing also silver in the presence of ammonium ions.

The samples of sterile animal tissue may then, for example, be placed in an aqueous solution containing ammoniacal silver sulfadiazine. The source of the ammonium ions may vary, although one preferred source of the ammonium ions is $NH_4OH$ in solution. The samples are placed in solution for the desired length of time, and then removed and allowed to partially dry. Complete drying is not desirable, as such complete drying may resultin shrinking, hardening, and cracking of the samples, rendering them unsuitable for use in burn and wound therapy. Following partial drying, the samples are placed in storage under sterile conditions.

Soaking is not the only method of incorporation of ammoniated silver sulfadiazine in the animal tissue. For example, it is possible to spray previously prepared samples of animal tissue with ammoniated solutions of silver sulfadiazine. The contacting of the ammoniated silver sulfadiazine to the animal tissue results in incorporation within the tissue matrix as previously described, and the subsequent method of storage and handling is identical.

In use as a wound covering, the ammoniated silver sulfadiazine incorporated animal tissue is directly applied to the burn or wound, and allowed to remain in contact with the burn or wound surface for the course of the therapy. The treatment of wounds or burns using such wound covers or dressings results in greater protection and survival against bacterial infection.

The following examples point out with more specificity the practices and advantages of the practices of the invention.

EXAPLE I

8×10 cm. patches of pigskin were soaked in 100 ml. of 10 μmol/ml solutions of sodium sulfadiazine. The patches are soaked for 4 days (shorter exposure to sodium sulfadiazine tended to yield a less effective product), after which the patches are blotted dry on 4×4 gauze squares. The patches are then placed in 100 ml of 5 μmol/ml solutions of $AgNo_3$ for 10 minutes. After such treatment in $AgNO_3$ solution, the pigskin was washed four times with distilled water.

In order to determine the amount of sulfadiazine and $Ag^+$ present in the tissue samples, assays employing standard techniques are used. Sulfadiazine content was determined by the method of Barathon & Marshall, and $Ag^+$ content is determined by performing red pyrogallol colorimetry. Such assays revealed that 0.5 $\mu mol/cm^2$ of sulfadiazine was available in a pigskin sample, while 0.83 $mol/cm^2$ of $Ag^+$ are available. This suggests that some silver becomes bound to protein molecules in the pigskin, in addition to forming silver sulfadiazine compounds.

The protein molecules to which the silver is bound are, presumably, collagen, see Fox, Modak and Sanford, "Silver Treated Graft Materials for Covering of Infected Burn Wounds, "*J. Ann. Chir. Plast.* 1979, 24, pp. 265-67.

EXAMPLE II

The efficacy of pigskin samples having silver sulfadiazine incorporated therein was tested, and compared to a standard wound dressing containing $Ag^+$ in the absence of sulfadiazine.

Samples of pigskin were prepared according to the method set forth in Example I. Discs of treated pigskin measuring 1 cm. in diameter were cut from such samples, and placed upon culture media containing colonies of Pseudomonas Aeruginosa. It was observed that the samples of pigskin which contain silver sulfadiazine produce a zone of inhibition on such cultures measuring 16-17 mm. in diameter. In comparison, the commercially available pigskin wound covering known as MEDISKIN (product of Genetic Laboratories, Inc.), incorporated with silver but not silver sulfadiazine, produced a zone of inhibition of 12-13 mm. under identical conditions.

EXAMPLE III

In vivo experiments were performed to determine the efficacy of pigskin with incorporated silver sulfadiazine in accordance with the invention and compared with other wound covers.

Laboratory mice were divided into three groups, each containing five mice, and contact burns were caused by applying a heat source (hot plate) of 150° C. for five seconds to dorsa which had been shaven with an electric clipper. Burn eschar which formed was removed one hour post burn, and the wounds were seeded with a virulent strain of Pseudomanas Aeruginosa (Boston) bacteria. The infections were 0.1 ml of 0.6 O.D. at 600 NM innoculum. The wounds were then covered with one of three dressings: plain MEDISKIN (product of Genetic Laboratories, Inc.), MEDISKIN incorporated with silver, or pigskin with which has been incoporated silver sulfadiazine. The criterion observed was survival. Results are summarized in the following Table I:

TABLE I

| A. Pigskin + AgSD | | | B. MEDISKIN + $Ag^+$ | | | C. Plain MEDISKIN | | |
| --- | --- | --- | --- | --- | --- | --- | --- | --- |
| Days After Burn | Mortality Rate (# and % age) | | Days After Burn | Mortality Rate (# and % age) | | Days After Burn | Mortality Rate (# and % age) | |
| 1 | 0 | 0% | 1 | 2 | 40% | 1 | 2 | 40% |
| 2 | 0 | 0% | 2 | 5 | 100% | 2 | 5 | 100% |
| 3 | 0 | 0% | 3 | 5 | 100% | 3 | 5 | 100% |
| 4 | 1 | 20% | 4 | 5 | 100% | 4 | 5 | 100% |
| 5 | 1 | 20% | 5 | 5 | 100% | 5 | 5 | 100% |

EXAMPLE IV

A second comparison of plain MEDISKIN and pigskin with which silver sulfadiazine is incorporated was performed. The group contained three mice each, and conditions were the same as those described in Example III. Results of this experiment are set out in TABLE II:

TABLE II

| Pigskin + AgSD | | | Plain MEDISKIN | | |
| --- | --- | --- | --- | --- | --- |
| Days After Burn | Mortality (% and #) | | Days After Burn | Mortality (% and #) | |
| 1 | 0% | 0 | 1 | 0% | 0 |
| 2 | 0% | 0 | 2 | 33% | 1 |
| 3 | 0% | 0 | 3 | 67% | 2 |
| 4 | 0% | 0 | 4 | 67% | 2 |
| 5 | 0% | 0 | 5 | 67% | 2 |
| 6 | 0% | 0 | 6 | 67% | 2 |
| 7 | 33% | 1 | 7 | 67% | 2 |
| 8 | 33% | 1 | 8 | 67% | 2 |
| 9 | 33% | 1 | 9 | 67% | 2 |

EXAMPLE V

In vivo observation of the bacteriocidal properties of $AgNO_3$ soaked pigskin and pigskin with incorporated silver sulfadiazine was observed.

Fifteen female rats received burn wounds from a metal hot plate applied to shaved dorsa, producing wounds measuring approximately 4×8 cm. Approximately 24 hours later wound eschars were removed and the wounds were seeded with 0.5 ml samples of Pseudomonas Aeurigimosa (Boston) bacteria, of 0.60 O.D. One hour later, wound covers were applied to 12 of the mice: three of the mice had wounds covered with pigskin which had been soaked in 0.1M $AgNO_3$ for one hour; a second group received wound covers of pigskin soaked in 0.01M silver sulfadiazine solution for one hour; the third group's wounds were covered with plain pigskin which had not been soaked in any solution; a fourth group received covers of pigskin soaked in distilled water, and three rats in the fifth group had wounds left opened. Those rats which received no wound cover and those which received wound covers soaked in water served as controls for initial infection. The rats were observed from day to day, and those rats which survived more than nine days, when dressings were changed, were observed for infection. The results of these three groups (plain pigskin, $AgNO_3$ pigskin, and silver sulfadiazine pigskin) follow:

| | SUBJECT | | |
|---|---|---|---|
| Material | #1 | #2 | #3 |
| Plain Pigskin | Died: Pseudomonas- 5 days | Died: Pseudomonas- 6 days | Died: 13 day (Pseudomonas suspected) |
| $AgNO_3$ Pigskin | Died: Proteus- 5 days | Died: Pseudomonas- 6 days | Severe Pseudomonas infection |
| Silver Sulfa- diazine pigskin | Mild Proteus infection | Mild Proteus infection | No infection |

No Pseudomonas infection was discovered in any of the three mice treated with silver sulfadiazine soaked pigskin. Mild proteus infections were discovered in two of them, but the infections were not severe enough to cause mortality. Infection by Pseudomonas was also observed to those rats which had been treated with pigskin soaked in water.

EXAMPLE VI

The efficacy of pigskin with incorporated silver sulfadiazine in ammonia solutions were tested. Samples of pigskin with incorporated silver sulfadiazine in ammonia solutions as described in Example I are prepared, and tested for antibacterial activity. The test involved the use of standard circular disks which were cut from the samples, and placed upon blood agar plate cultures infected with *Pseudomonas aerugenosa*. Comparison tests were run with circular disks of the same size, which had been impregnated with a combination of sodium sulfadiazine and silver nitrate ($NaSD+AgNO_3$), ammonium hydroxide and, as a control, pigskin samples with no impregnated salts. The results are tabulated in Table I.

TABLE I

In Vitro Efficacy of Wound Covers Impregnated with Various Substances

| Substance | Zone of Inhibition |
|---|---|
| $NaSD + AgNO_3$ | 18 mm. |
| AgSD in ammoniated solution | 24 mm. |
| $NH_4OH$ | 0 mm. |
| None | 0 mm. |

The results clearly indicate the superiority of the pigskin tissue in which silver sulfadiazine in ammoniated solution is incorporated with the pigskin.

EXAMPLE VII

The in vivo efficacy of pigskin incorporated with ammoniated silver sulfadiazine was examined.

Swiss mice were anesthetized, and 2×3 cm areas or dorsa were burned on hot plates at 150° C. followed by excision of the burn eschar and infection with $10^7$ concentrations of *Pseudononas aeruginosa*. The mice were divided into groups, and received burn wound covers as follows: untreated pigskin, and pigskin which had been soaked in a solution of ammoniated silver sulfadiazine, as detailed in Example I. Additionally, a third group of mice received applications of silver sulfadiazine cream which had not been prepared in ammoniated solution. The criterion observed was survival—i.e., the mice were observed at two-day intervals, and the percentage of mortality was calculated with the results tabulated as follows.

TABLE II

In Vivo Efficacy of Silver Sulfadiazine

| | % Mortality | | |
|---|---|---|---|
| Wound Cover | 2 days | 4 days | 6 days |
| Untreated pigskin | 100 | 100 | 100 |
| Pigskin treated with silver sulfadiazine in ammonium hydroxide | 0 | 0 | 33 |

Those mice which received non-ammoniated silver sulfadiazine received it in the form of 1% silver sulfadiazine cream administered to the top of untreated pigskin wound covers. Such mice showed a mortality rate of 80% over the same six-day period.

EXAMPLE VIII

To test the in vivo efficacy of pigskin with ammoniated silver sulfadiazine incorporated therein, animal experiments were performed.

Female Swiss mice were anaesthetized, and 2×3 cm. areas of dorsal skin were burned at 150° C., using a hotplate. After one hour, 1.5 $cm^2$ of burn eschar was removed from each wound, and 0.03 D cultures of Pseudomonas aeruginosa were swabbed into the wounds. After an incubation period of one hour, pieces of pigskin measuring 2×3 cm. were used to cover the wounds. This pigskin had either been treated with ammoniated silver sulfadiazine, silver sulfadiazine cream (silvadene), or was left untreated. The criteria observed over a period of six days was survival. The relevant data is summarized below.

| | % Mortality (Days Postburn) | | | | | |
|---|---|---|---|---|---|---|
| Pigskin | 1 | 2 | 3 | 4 | 5 | 6 |
| Untreated | 0 | 60 | 100 | 100 | 100 | 100 |
| Ag SD cream | 0 | 0 | 50 | 50 | 100 | 100 |
| Ammoniated Ag SD | 0 | 0 | 0 | 0 | 10 | 10 |

EXAMPLE IX

Additional in-vitro experiments were performed to determine the zone of inhibition of pigskin with incorporated ammoniated silver sulfadiazine. Standard circular disks were cut from impregnated dressings and tested for antibaceterial activity against Pseudomonas aeruginosa on blood agar plate cultures. As controls, identical circular disks with $AgNo_3$ and $NH_4OH$ were prepared. The zones of inhibition are compared below:

| | Zone: |
|---|---|
| Ammoniated AgSD | 30 mm. |
| $AgNO_3$ | 12 mm. |
| $NH_4OH$ | 0 mm. |

EXAMPLE X

The incorporation of silver sulfadiazine in homografts, and its subsequent retention was tested.

Animal skin homografts were cut into 2 $cm^2$ pieces, and then soaked in 4% ammoniacal, $^{110}AGSD$ for four hours. Following soaking, the homograft samples were dried at room temperature, in the dark, until the ammonia was driven off.

Pieces were then divided into two groups, one of which was washed five times with water, and the other remained untreated. The specimens were then tested, for levels of incorporation of silver sulfadiazine, and zones of Inhibition. The results were summarized below:

|  | Drug Level | Zone of Inhibition |
| --- | --- | --- |
| Washed homograft | 0.21 mole/mg | 25 mm. |
| Unwashed homograft | 0.24 mole/mg | 25 mm. |

What is claimed is:

1. A method for preparing animal tissue for use as burn or wound dressings comprising soaking animal tissue in an aqueous solution containing soluble sulfadiazine, so as to incorporate sulfadiazine in said tissue, soaking the sulfadiazine incorporated tissue in a solution containing silver nitrate under conditions causing in situ formation of silver sulfadiazine in said tissue, and then rinsing and partially drying the silver sulfadiazine incorporated tissue.

2. A method as in claim 1, wherein said animal tissue is pigskin.

3. A method as in claim 1, wherein said animal tissue is amniotic tissue.

4. A method as in claim 1, wherein said animal tissue is human skin.

5. A method for the treatment of burns and/or wounds, comprising applying the product of claim 1 to burns and/or wounds.

6. An animal tissue product having silver sulfadiazine incorporated in situ therein, in accordance with the method of claim 1.

7. A pigskin tissue product having silver sulfadiazine incorporated in situ therein, in accordance with the method of claim 1.

8. An amniotic tissue product having silver sulfadiazine incorporated in situ therein, in accordance with the method of claim 1.

9. A human skin tissue product having silver sulfadiazine incorporated in situ therein, in accordance with the method of claim 1.

10. The method of claim 1, wherein said soluble sulfadiazine is sodium sulfadiazine.

* * * * *